United States Patent [19]
Potratz

[11] Patent Number: 5,351,685
[45] Date of Patent: Oct. 4, 1994

[54] CONDENSED OXIMETER SYSTEM WITH NOISE REDUCTION SOFTWARE

[75] Inventor: Robert S. Potratz, Lenexa, Kans.

[73] Assignee: Nellcor Incorporated, Pleasanton, Calif.

[21] Appl. No.: 740,362

[22] Filed: Aug. 5, 1991

[51] Int. Cl.$^5$ ............................................. A61B 5/00
[52] U.S. Cl. ................................ 128/633; 128/664; 128/665; 128/666; 356/41
[58] Field of Search ........ 128/633, 664, 665, 666–667; 356/39, 41

[56] References Cited

U.S. PATENT DOCUMENTS

| | | | |
|---|---|---|---|
| 4,086,915 | 5/1978 | Kofsky et al. | 128/633 |
| 4,653,498 | 3/1987 | New, Jr. et al. | 128/666 X |
| 4,800,885 | 1/1989 | Johnson | 128/633 |

*Primary Examiner*—Angela D. Sykes
*Attorney, Agent, or Firm*—Townsend and Townsend Khourie and Crew

[57] ABSTRACT

A compact pulse oximetry system which separates the combined signal into its respective AC and DC components. By separating the signal into AC and DC components, a smaller order bit A/D converter may be used while still maintaining signal accuracy. Instead of using the combined signal to calculate the oxygen saturation content, the system microprocessor computes the Ratio of Ratios using the derivative of the separated AC component of the diffused signal to calculate the oxygen saturation of the measured fluid. To calculate the Ratio of Ratios, a ratio of the derivative value of the separated AC component is used. Instead of taking a single sample between the peak and valley of the signal, the oximeter system samples each value. To decrease the effect of system noise, a linear regression is performed over each sample.

30 Claims, 14 Drawing Sheets

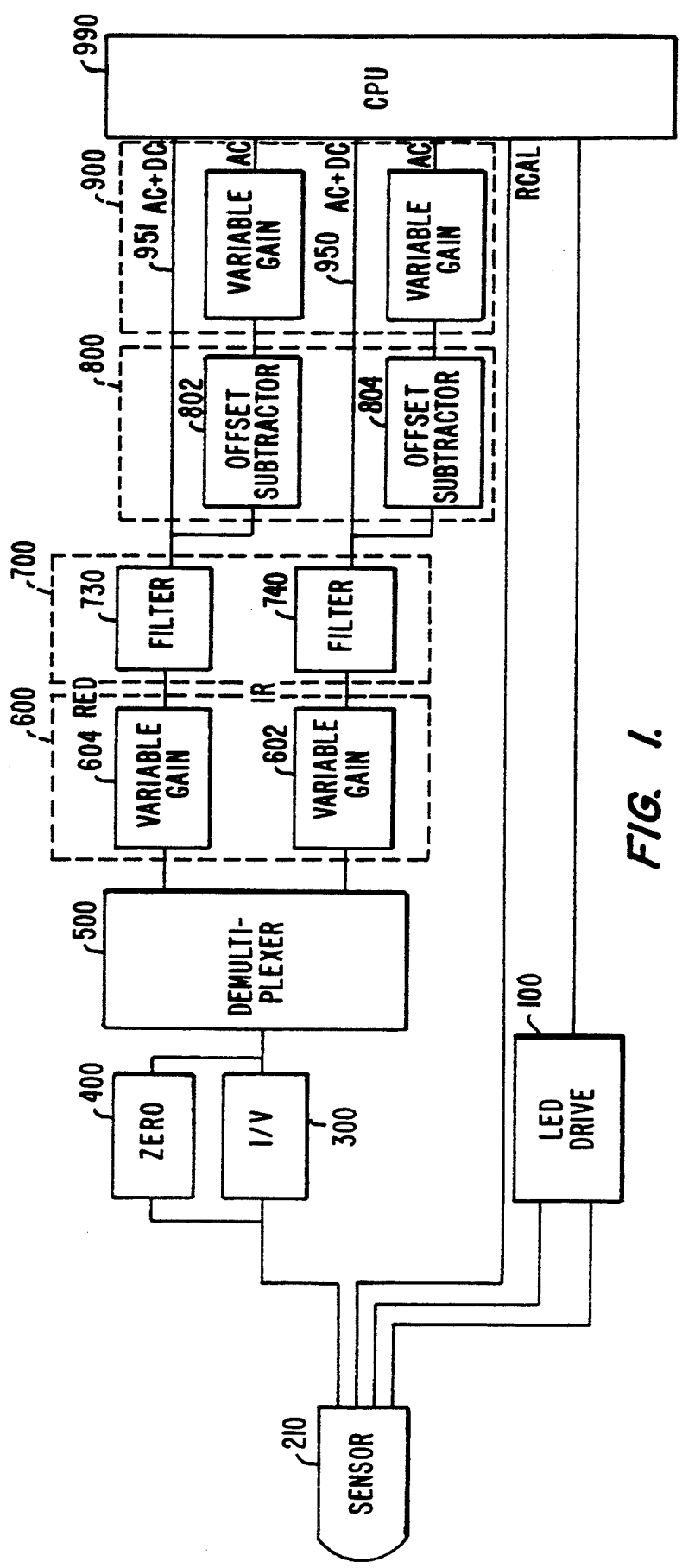

FIG. 2D.
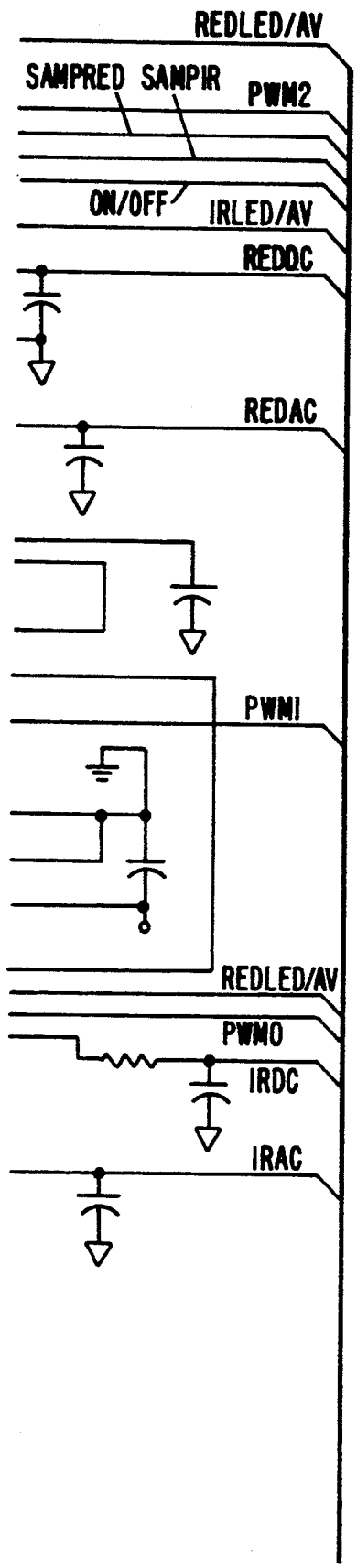
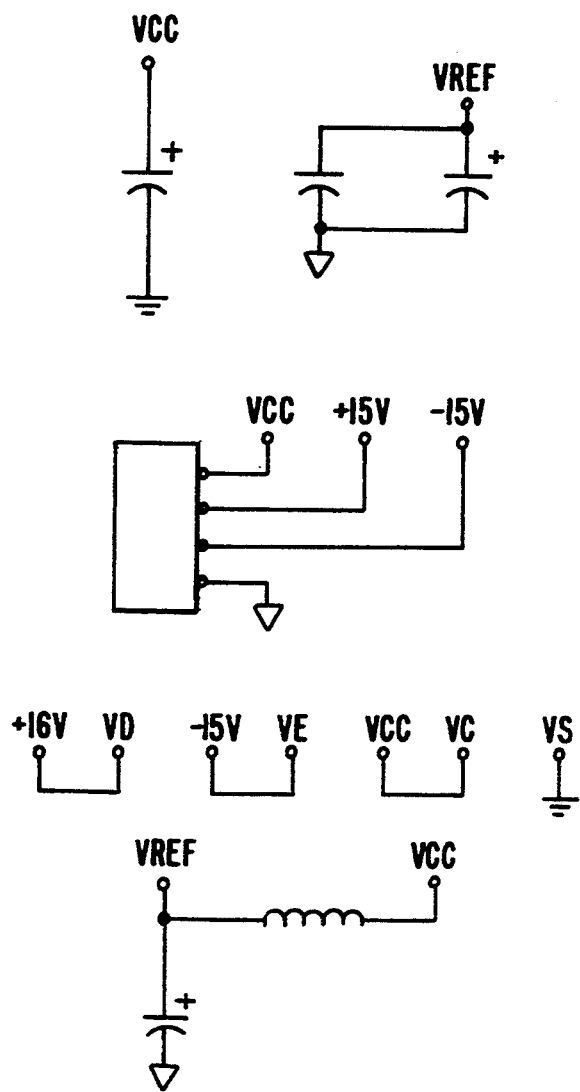

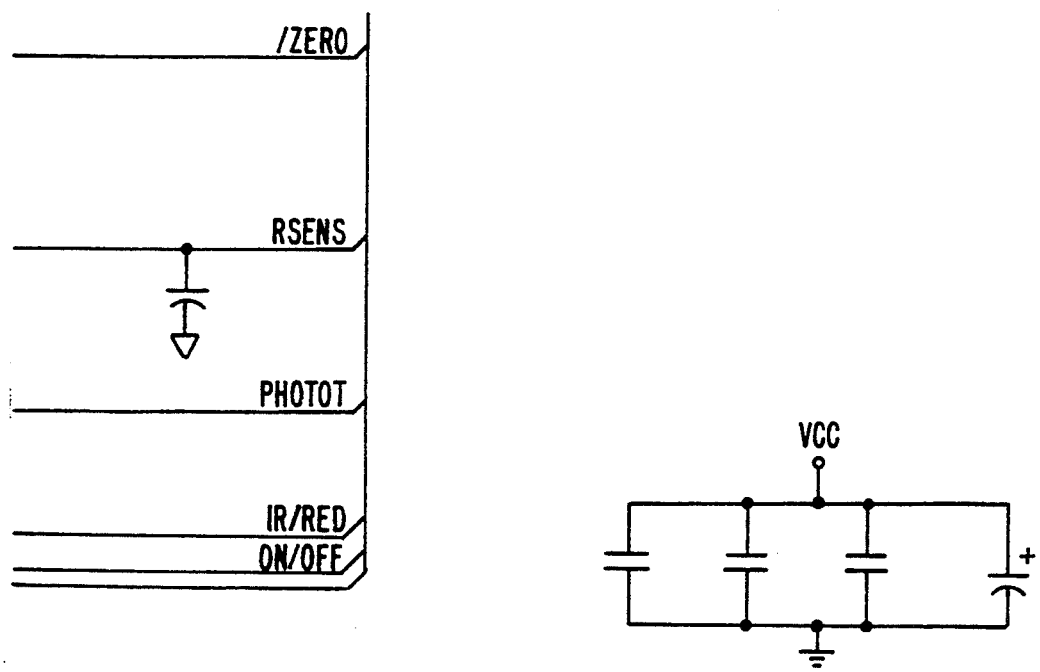
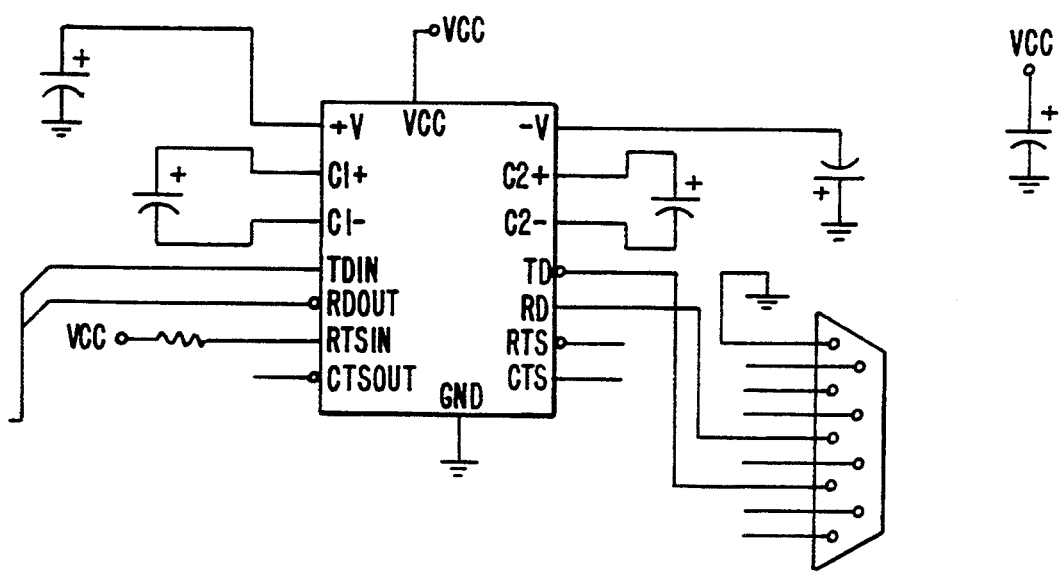
FIG. 2H.

CONDENSED OXIMETER SYSTEM WITH NOISE REDUCTION SOFTWARE

BACKGROUND OF THE INVENTION

Certain components in the blood absorb light more strongly at different wavelengths. For example, oxyhemoglobin absorbs light more strongly in the infrared region then in the red region. Therefore, highly oxygenated blood having a high concentration of oxyhemoglobin will tend to have a high ratio of optical transmissivity in the infrared region. The ratio of transmissivities of the blood at red and infrared wavelengths can be employed in calculating oxygen saturation of the blood.

This principle has been used in oximeters for monitoring oxygen saturation of the blood, as for example, in patients undergoing surgery. Oximeters for this purpose may include a red and infrared light emitting diode together with a photodetector. The oximeter is typically clamped to an appendage of the patient's body, such as an ear or finger. The oximeter directs a beam of red and infrared light of known frequency and wavelength into the appendage. A sensor on the other end of the appendage receives the diffused light. Knowing the change in wavelength, frequency, and intensity of the diffused light beam, the oximeter can quickly determine the oxygen saturation level of the patient.

The diffused light signal received by the photodetector is an analog signal which includes both an AC and DC component. The diffused light signal includes an AC component which reflects the varying optical absorption of the blood due to variance in the volume of the blood due to the pulsatile flow of blood in the body. The diffused signal also includes an invariant or DC component related to other absorption, such as absorption by tissues other than blood in the body structure.

The diffused analog light signal is converted into a digital signal. The digital representation is used by the oximeter system microprocessor for processing the oxygen saturation level. Because calculation of the oxygen saturation is critical for determining the status of the patient, a high degree of accuracy is required for the digital representation of the diffused analog light signal. A problem in converting from an analog to a digital representation of the signal is that the DC component is so much larger than the AC component of the diffused signal. To encompass both the AC and DC components of the entire diffused signal requires using a 16 bit A/D converter. Using a smaller A/D converter, for example an 8 bit A/D converter, would cut off the least significant bits of the signal, namely the AC component of the signal. Receiving an accurate representation of the AC component is critical, since it is the AC component of the diffused signal which reflects the oxygen absorption.

Because of the degree of precision necessary to accurately reflect the AC component of the signal, currently available oximeter systems typically uses a 16-bit A/D converter. A 16 bit A/D converter may be four times as expensive as currently available microprocessors which include an 8 bit A/D converter and a pulse width modulator in a single chip. Since 8 bit does not give a sufficient degree of accuracy to encompass for oxygen absorption measurements, a combined 8 bit microprocessor A/D converter chips cannot be used. A separate 16 bit A/D converter must be used.

In addition to increasing the costs of the oximeter system, using a separate 16 bit A/D converter increases the size and power consumption of the system. Adding a separate 16 bit A/D converter adds to the size of the measurement system. Because the oximeter measurement system is connected to a patient and because the system is often moved between patient rooms, compactness of size of the pulse oximeter measurement system is highly desirable.

The digital representation of the diffused signal is used by the oximeter system microprocessor to calculate oxygen saturation level in the blood of a patient. The Ratio of Ratios, a variable used in calculating the oxygen saturation level, is typically calculated by taking the natural logarithm of the ratio of the peak value of the infrared signal divided by valley measurement of the red signal. The aforementioned value is then divided by the natural logarithm of the ratio of the peak value of the red signal divided by the value of valley measurement of the infrared signal.

The diffused signal is sampled several times during each period to determine the peak and valley measurement for each period of the waveform. In calculating the Ratio of Ratios, the peak value is assumed to be the high sample value during the period of the waveform. The valley measurement is assumed to be the low measured value. Although this method leads to a good estimate of the variable R, taking the peak and valley measurements over the entire time interval is prone to error since the sampling is taken between a single pair of points. This ignores variation in the signal between different pulses during the measured time interval.

A problem with choosing a single peak and valley measurement during a sampling interval, is corruption of the measurement by system noise. For example, patient motion of the oximeter during the sampling period may cause drift in the AC component of the signal. Also, ambient light or electrical noise may increase system noise. If the added noise on the pulse creates a false peak or valley measurement during the sampling interval, this will cause an incorrect value for the Ratio of Ratios. An inexpensive, noise insensitive oximeter measurement system is needed.

SUMMARY OF THE INVENTION

The present invention provides a compact pulse oximeter probe which includes at least one narrow bandwidth light emitting diode and at least one photoelectric sensor. The signal measured by the photoelectric sensor has both an AC and DC component. Instead of using a high order 16 bit A/D converter to maintain signal accuracy, the present invention separates the AC and DC components and uses a smaller A/D converter. Instead of using the combined signal to calculate the oxygen saturation content, the system microprocessor computes the Ratio of Ratios using the derivative of the separated AC component of the diffused signal to calculate the oxygen saturation of the measured fluid.

The AC component is separated out by using a capacitor which is normally charged immediately after each valley of the AC sensor signal. The valley represents the DC portion of the AC sensor signal. By subtracting the voltage on the capacitor from the combined signal, only the AC component is left. A fixed DC offset is added to place the resulting AC signal in the middle of the range of the A/D converter.

Instead of taking a single sample between the peak and valley of the signal, the oximeter system samples multiple values. A derivative of the AC component is taken between each pair of sample values. This AC derivative value is used in calculating the Ratio of Ratios. Because the ratio of the derivative of the red and infrared signals is a straight line, a linear regression may be performed to decrease the effect of system noise.

The present invention also uses a pulse width modulator in the microprocessor to control the peak-to-peak values of both the red and infrared signals so that they extend across most of the range of the A/D converter to give maximum resolution. This can be done by controlling the intensity of the LED driver so that the average signal has the desired intensity. Because the red and infrared signals produce different levels of the detector signal, they are amplified differently. Alternatively, on the received end the signals can have the amplification factor controlled by the pulse width modulator.

By separating the AC and DC component of the diffused signal, a 16 bit A/D converter is not necessary to give an accurate representation of the AC component. Since a digital representation of the separated AC component can be accurately represented by an 8 bit A/D converter, a combination microprocessor analog to digital converter chip may be used. Using a combination microprocessor decreases system size and cost. Furthermore, using a single chip microprocessor decreases overall power consumption of the system.

A further understanding of the nature and advantages of the invention may be realized by reference to the remaining portion of the specification and the drawings.

BRIEF DESCRIPTION OF THE DRAWINGS

FIG. 1 is a block diagram of the oximeter measurement system according to the present invention.

FIG. 2A-2H are a circuit schematic of the oximeter measurement system of FIG. 1.

FIG. 2 shows the manner in which FIGS. 2A-2H are associated.

DESCRIPTION OF THE PREFERRED EMBODIMENT

Figure 2A:
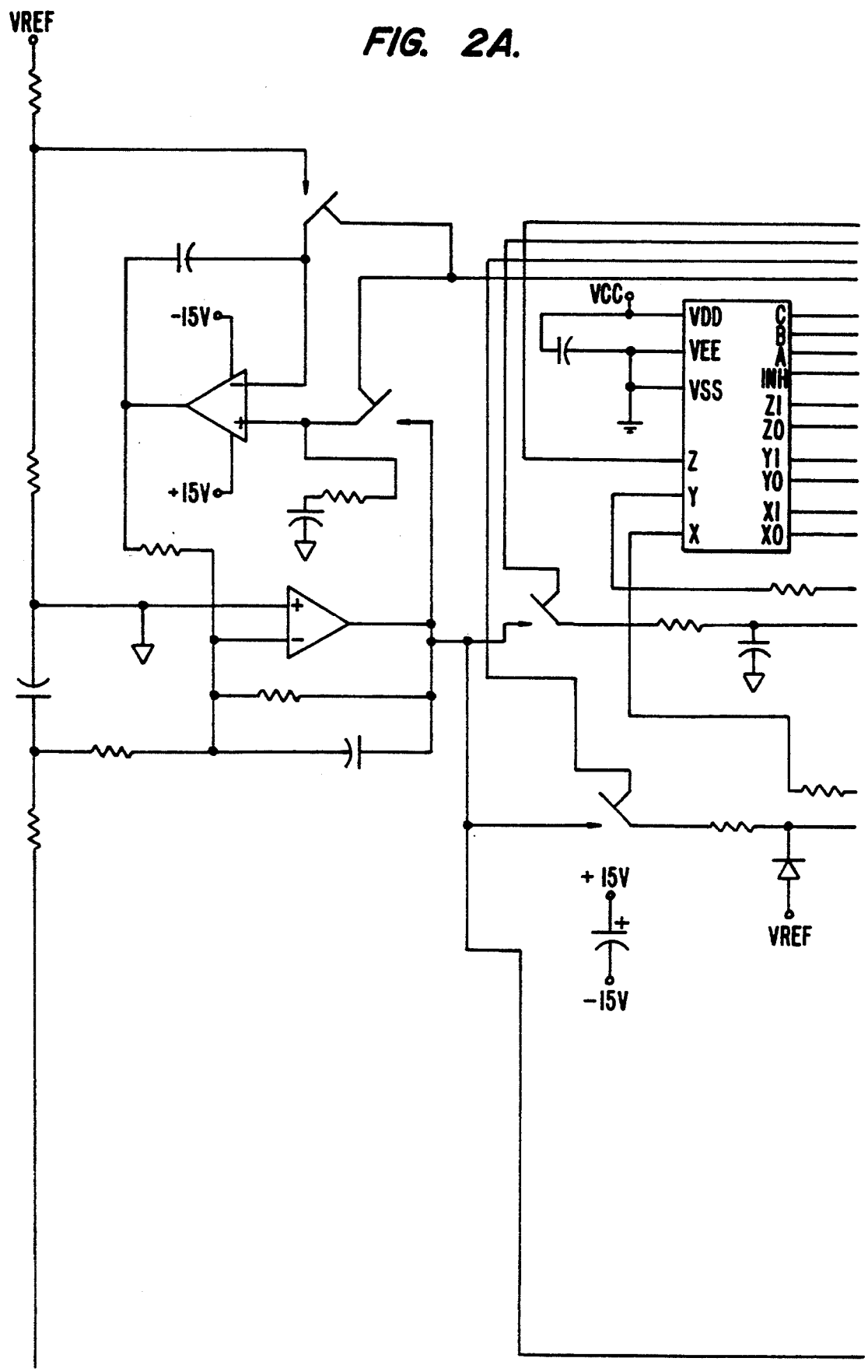
Figure 2B:
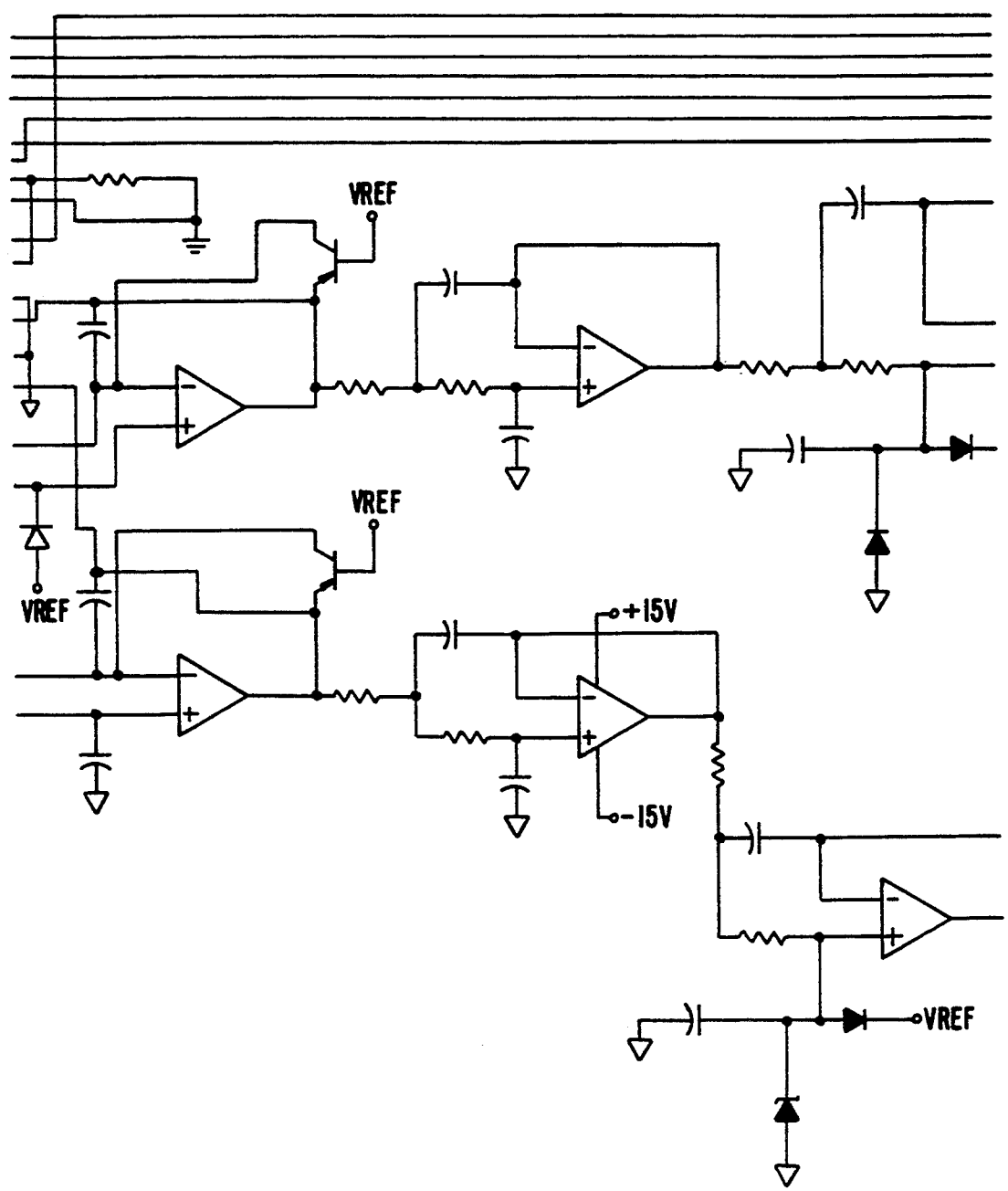
Figure 2C:
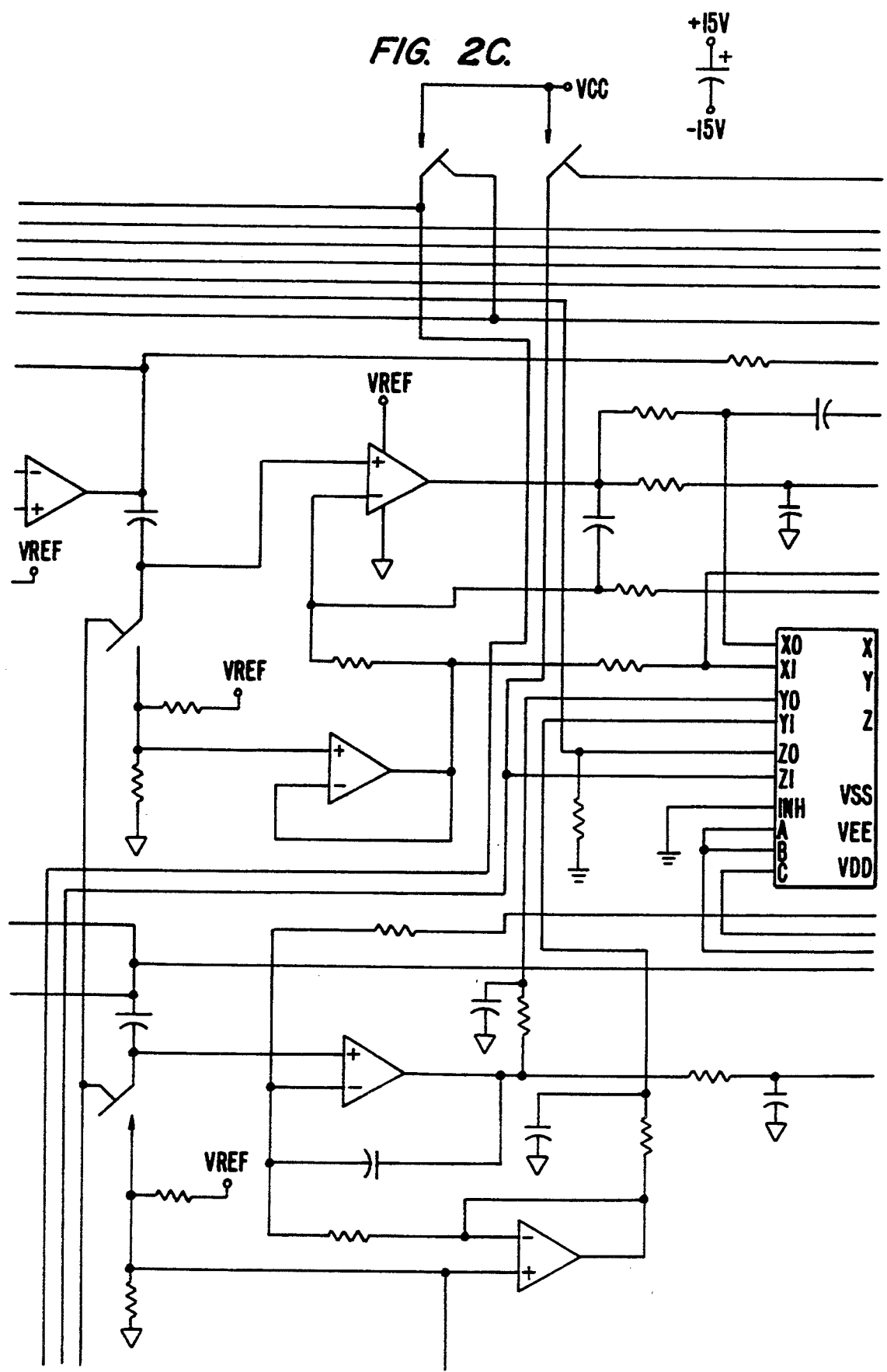
Figure 2E:
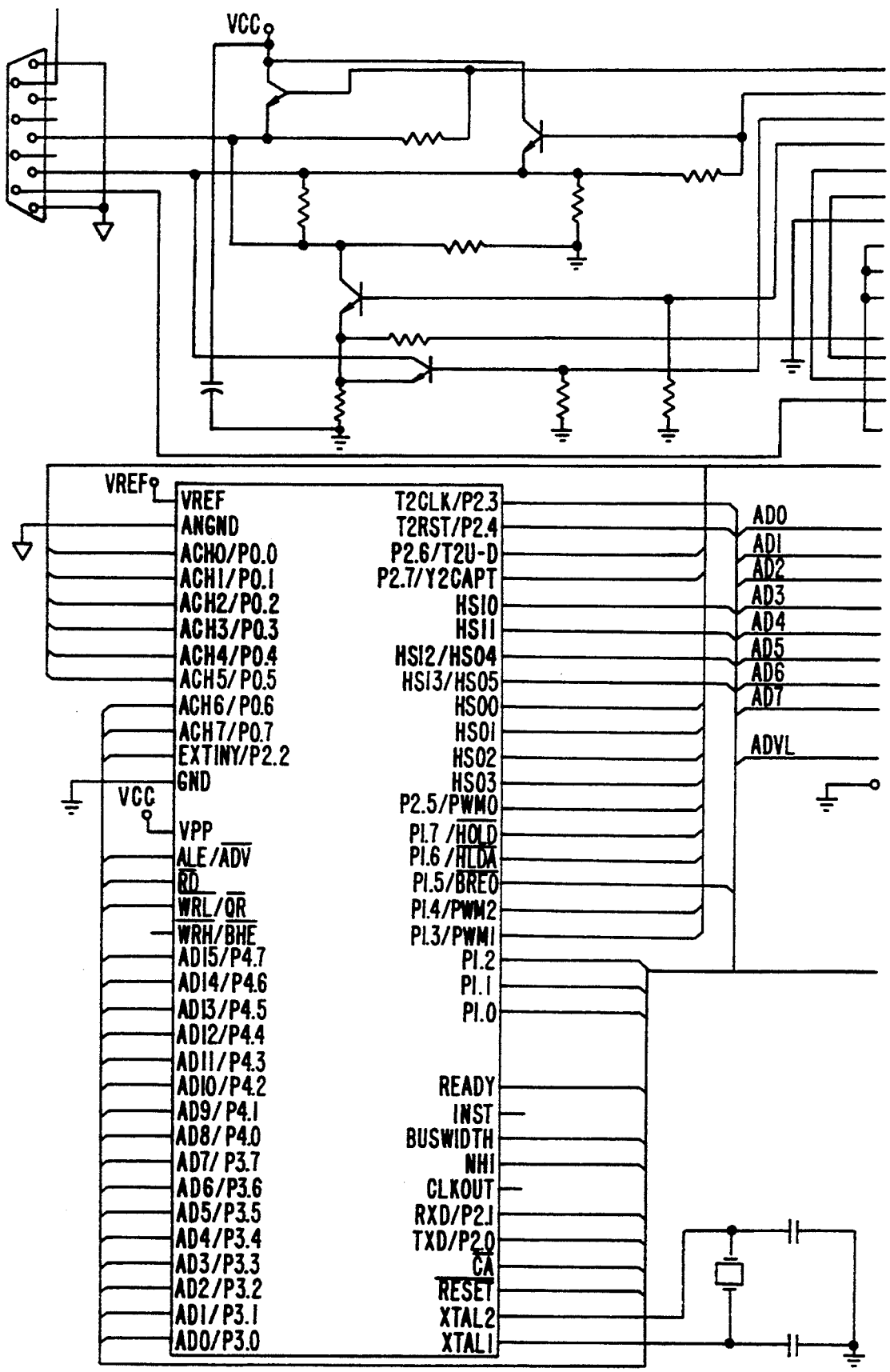
Figure 2F:
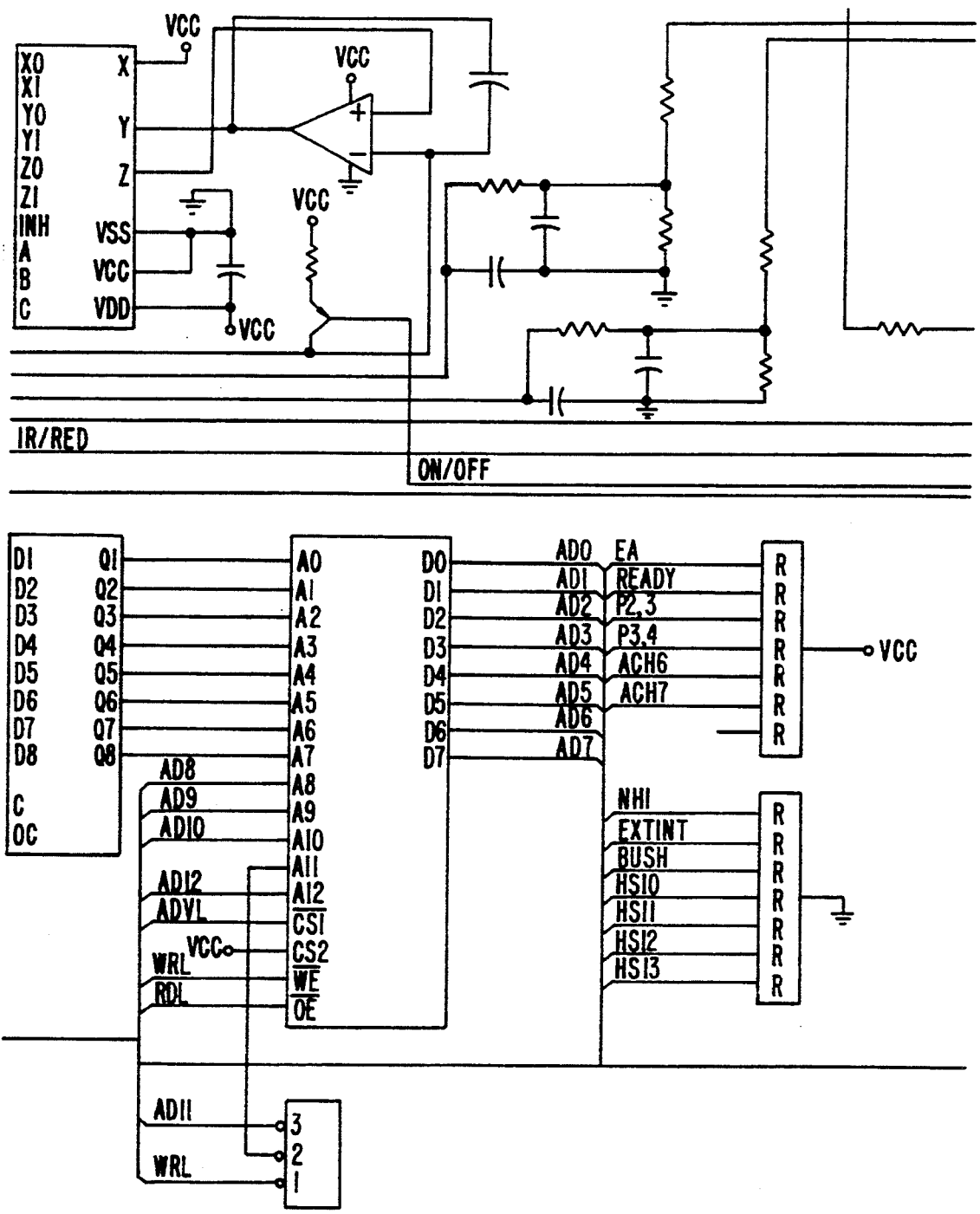
Figure 2G:
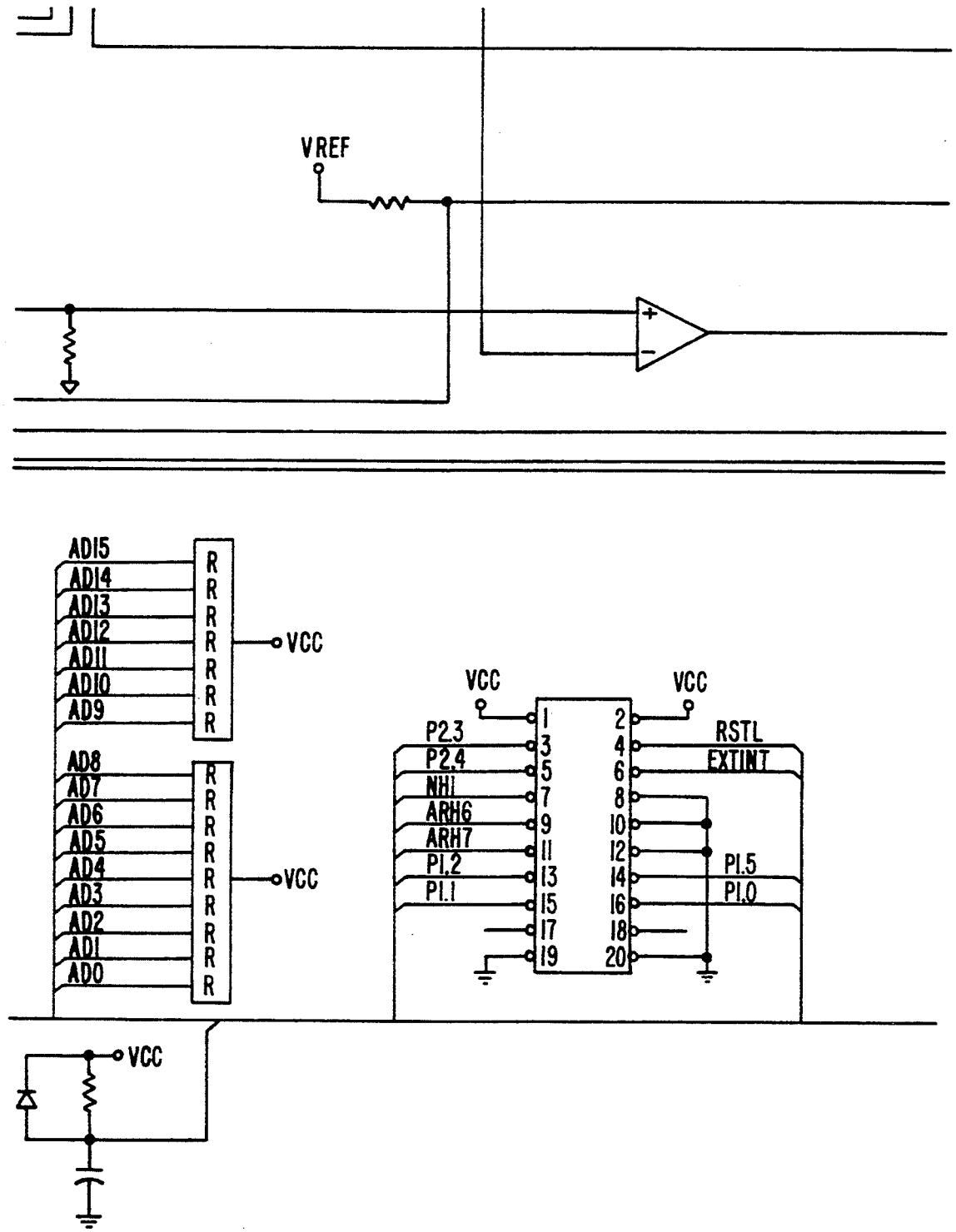

The present invention relates to an improved oximetry measurement system for measuring the blood constituents. The oximeter measurement system includes an oximeter optical probe typically comprised of two light emitting diodes, a photoelectric sensor, and a means for fastening the optical probe to an appendage. The first LED typically emits frequency in the infrared range. The second LED typically emits light in the red range of the spectrum.

The infrared and red light emitting diodes are switched on and off in an alternating sequence at a switching frequency far greater than the pulse frequency. The signal produced by the photodetector includes alternating portions representing red and infrared passing through the body structure. These alternating portions are segregated by sampling devices operating in synchronism with the red/infrared switching, so as to provide separate signals on separate channels representing the red and infrared light transmission of the body structure.

The oximeter probe is typically clamped to an appendage of the patient's body, such as an ear or finger. For each heartbeat, fresh arterial blood is pumped into the capillaries of the appendage. Light from the two LEDs is modulated by the pulsatile component of arterial blood thereby causing a periodic increase and decrease in the light intensity observed by the sensor. The oxygen saturation of hemoglobin in the pulsatile blood may be determined by the oximeter.

FIG. 1 illustrates a block diagram of the oximeter measurement system according to the present invention. The oximeter measurement system includes a Current/Voltage Converter Unit 300, a Zeroing Unit 400, a Demultiplexer 500, a Variable Gain Amplifier Unit 600, a Filtering Unit 700, an Offset Subtractor Circuit 800, a Second Variable Gain Amplifier Unit 900, and a Microprocessor 990. The output from the photoelectric sensor is fed into both the Current/Voltage Converter Unit 200 and the Zeroing Unit 300. When an LED signal value is received, the photoelectric output current is converted into a voltage by the Current/Voltage Converter Unit 200. When no LED signal value is received, the Zeroing Unit 300 zeroes the output of the Current-/Voltage Converter Unit 200.

The infrared and red light emitting diodes are switched on and off in an alternating sequence. These alternating portions must be segregated so as to provide separate signals on separate channels. A Demultiplexer 400 selects whether the sensed current is a infrared signal or a red signal. Both the infrared and red signal are input into the Variable Gain Amplification Unit 400. Amplifier 402 typically amplifies the infrared signal. Amplifier 404 amplifies the red signal. Different amplification factors may be used. The amplification factors are controlled by a pulse width modulation signal from processor 990.

Both the infrared and red LED signals are fed into a Filtering Unit 600 for reducing noise at the switching frequency. The filtered signal is fed into an Offset Subtractor Circuit 700. The Offset Subtractor Circuit 700 separates the AC component of the combined signal from the combined signal. The separation is accomplished by tracking the AC component of the combined signal through a capacitor periodically charged to the DC value.

The AC component is passed through a Second Variable Gain Amplification Unit. The AC component and combined AC and DC signal are amplified by different amplification factors. The amplified signal is fed into a Microprocessor Unit 990 which computes the oxygen saturation level in the blood. Both the AC signal (lines 952,953) and the combined AC and DC signal (lines 950, 951) are fed in analog form to processor 990, which uses its internal 10 bit A/D converter to convert them into digital form. Calculating the oxygen saturation level is done by the software in the microprocessor unit 990. The microprocessor uses the derivative of the separated AC component of the combined signal to calculates the Ratio of Ratios. Knowing the Ratio of Ratios allows for calculation of the oxygen saturation content.

The Current/Voltage Divider

Figure 3:
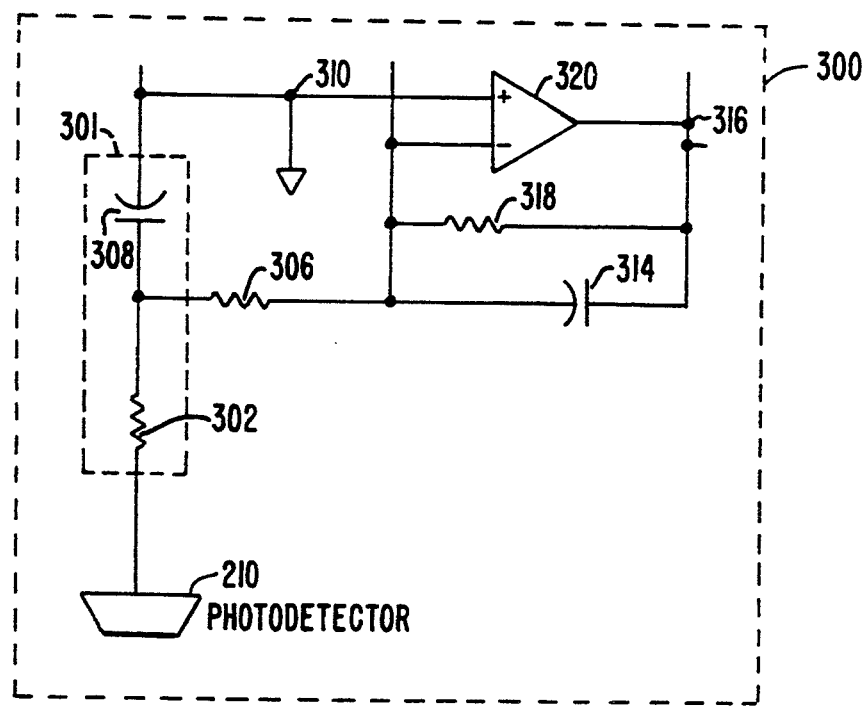
FIG. 3 is a circuit schematic of the Current to Voltage Converter according to FIG. 2.

The oximeter probe photodetector 210 senses a current in response to the infrared or red light source projected through an appendage. The sensed current is transformed into a voltage via the Current to Voltage Converter 300. FIG. 3 is a circuit schematic of a Current to Voltage Converter 300 according to the present invention. The current on line 302 from the photodetector 210 is input into a resistor capacitor network 301 comprised of resistor 302 and capacitor 308. The resistor capacitor network 301 filters high frequency noise from the photodetector signal.

The input terminals of amplifier 320, capacitors 308, 314, resistors 306 and 318 are all connected to node 310 which provides a virtual ground. Thus when current flows across resistor 306, a voltage drop occurs across capacitor 308 which filters the input signal. Current flowing from resistor 306 across resistor 318 provides the current to voltage conversion. Since node 310 acts as a virtual ground, current flowing into the input terminal of amplifier 320 adjusts to take up any current across resistor 318. The voltage drop across resistor 318 is output at node 316 of amplifier 320 and is proportional to the sensed current.

The Zeroing Circuit

Figure 4:
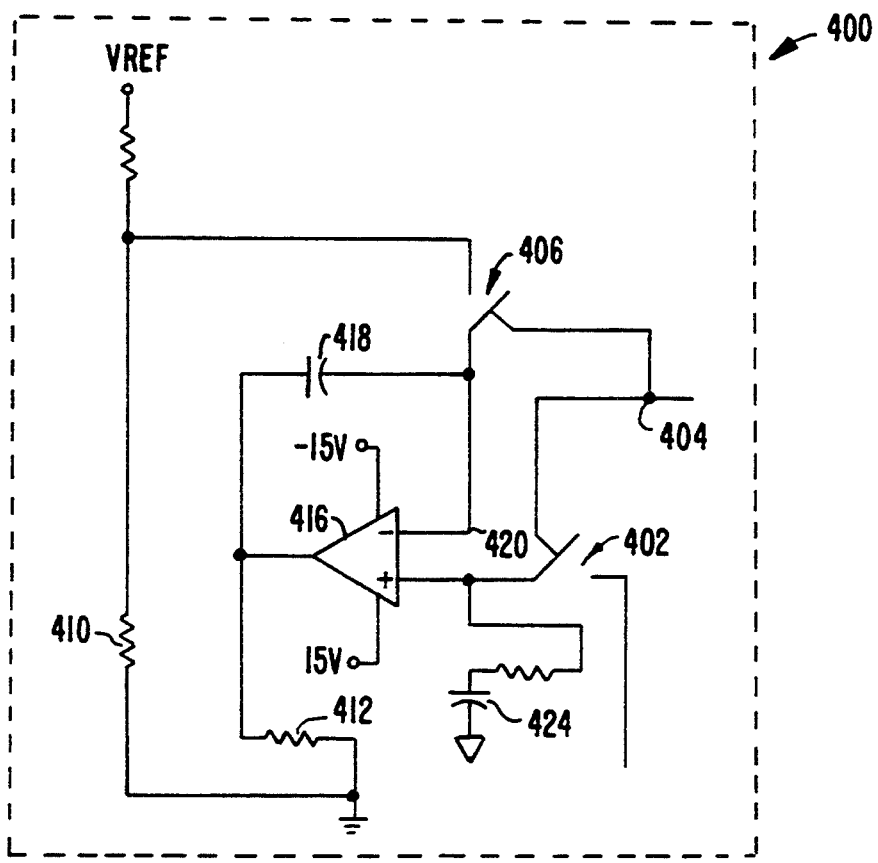
FIG. 4 is a circuit schematic of the Zeroing Circuit of FIG. 2.

Current flowing from the output node 316 of the Current/Voltage Converter is input into the Zeroing Circuit 400. A circuit schematic of the Zeroing Circuit is illustrated in FIG. 4. The purpose of the Zeroing Circuit 400 is to prevent a voltage at output node 316 when the respective LED is off. Current flow in photodetector 210 may occur due to residual light or from the LED circuit not being fully turned off.

The output signal on line 317 of the Current/Voltage Converter is input to a switch 402. A second switch 406 is connected to switch 402. Both switches 402 and 406 are tied together so that they both close or open simultaneously. FET switches 402 and 406 should both have their leads aligned so that both of their drains, or alternatively both of their sources, face amplifier 416. By positioning their leads in this manner, charge injection is minimized.

Both switches 402 and 406 are coupled to the input terminals of an inverting amplifier 416. When switches 402 and 406 are closed, a capacitor 424 begins charging to the output value of node 316 of the Zeroing Circuit. Increasing the voltage at positive terminal 412 of amplifier 415 results in an increased voltage at negative terminal 420. Creating a positive voltage on node 420 causes current to flow into capacitor 418 and produces current flow through resistor 410, which is connected to virtual ground 310.

Thus, when both switches 402, 406 are closed, a positive current flows through resistor 412 causing current to into the virtual ground node 310. This positive current flow results in a decrease in voltage on output node 316 of the Current/Voltage Converter 300. Thus when switches 402,406 are closed, a positive voltage on the output node 316 of the Current/Voltage Converter 300 generates a current which forces output node 316 of the amplifier 320 to zero.

When both switches 402, 406 are open, the voltage stored on node 422 before opening of the switch will be held there by the capacitor 424. This voltage offset gets rid of the offset in the amplifier 416. Similarly since switch 406 is open, there is no discharge path for the charge stored on node 420. The current going through resistor 412 will continue to flow, at the level flowing immediately before the switch 406 was opened. Thus the current which sets output node 316 to zero is injected with the current coming in. So the output node 316 is going to react as if there was no current coming in initially. The current going through resistor 412 is going to cancel the ambient current.

The Demultiplexer

Figure 5:
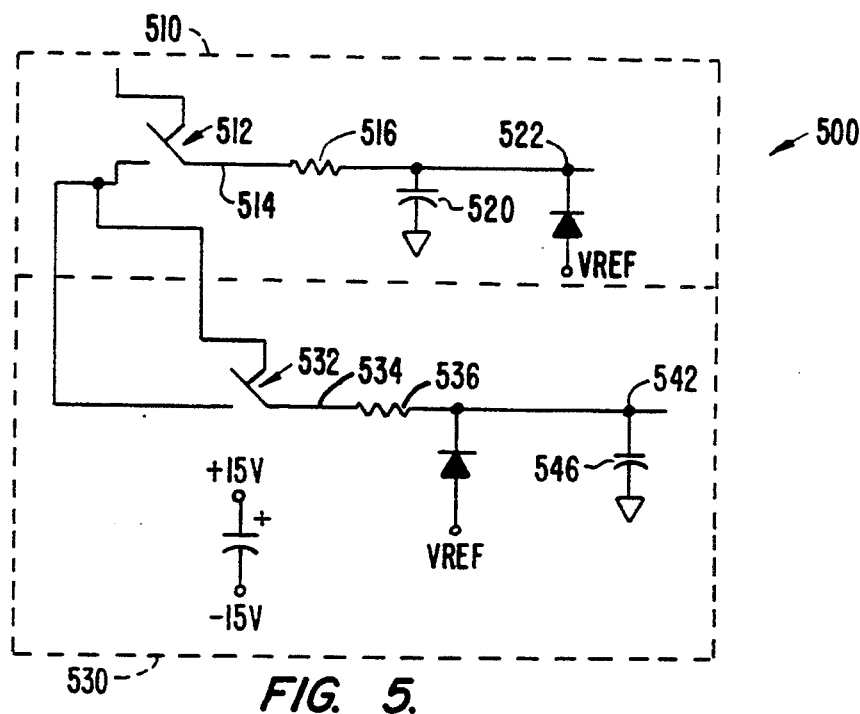
FIG. 5 is a circuit schematic of the Demultiplexer of FIG. 2.

FIG. 5 is a circuit schematic of the Demultiplexer Block 500 according to the present invention. The Demultiplexer Block has two separate demultiplexers 510 and 530 for the infrared and red signals respectively. The red and infrared demultiplexers are functionally equivalent. The red signal demultiplexer 530 is described for illustration.

The red signal demultiplexer 530 is comprised of a switch 532, and a resistor 534 and capacitor 540 in series. The timing of the opening and closing of switch 532 is controlled by the microprocessor. After the red signal stabilizes switch 532 is closed allowing the red signal to pass from node 316 to node 532. Series resistor 534 and capacitor 540 filter the sampled red signal.

The Variable Gain Amplifier

Figure 6:
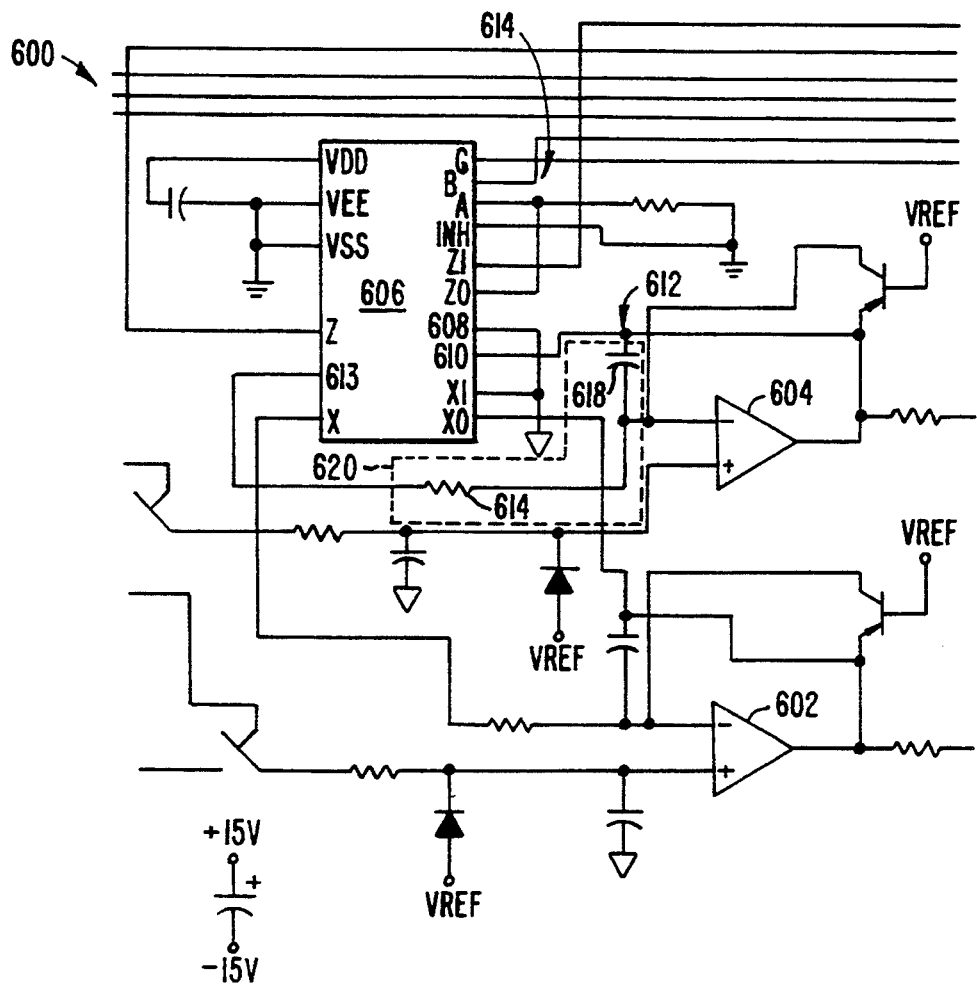
FIG. 6 is a circuit schematic of a Variable Gain Controlled Amplification Unit of FIG. 2.

FIG. 6 is a circuit schematic of a Variable Gain Controlled Amplification Unit 600 according to the present invention. The variable gain amplifier 600 amplifies the detected LED signals with the amount amplification controlled by the pulse width modulator 991 of the microprocessor 990.

The Variable Gain Controlled Amplification Unit is comprised of a pair of amplifiers 602, 604 coupled to a switch 606. In the illustrated embodiment, amplifier 604 amplifies the red LED signal and amplifier 602 amplifies the infrared LED signal. Both amplifiers are functionally equivalent. The red variable gain amplifier is described for illustration purposes.

The output from both amplifiers 602, 604 are input into a switch 606. The switch 606 contains three single pole double throw switches. The output of amplifier 604 is input into pole 608 and pole 610 of the switch 606. Pole 608 is normally connected to ground. Pole 610 is normally connected to the output of the amplifier 604. Thus the output of amplifier 604 at node 612 is alternately switched between ground and the value of the amplifier output.

The timing control of the switching is controlled by the pulse width modulator 991. The pulse width modulator signal is the input at node 616 of switch 606. The pulse width modulator signal at node 616 controls how long node 613 is connected to ground and the amplifier output.

Thus the pulse width modulator signal can be varied to effect how long the pulse width is on or off. For example, if the pulse width modulator signal on line 614 is off $\frac{2}{3}$ of the time and on $\frac{1}{3}$ of the time, the signal at node 613 would be connected to ground for $\frac{2}{3}$ of the duty cycle of the pulse width modulator and connected to the output of the amplifier for $\frac{1}{3}$ of the duty cycle of the pulse width modulator. The switch output signal at node 613 is input into a resistor capacitor network 620 comprised of a resistor 614 and a capacitor 618. The resistor capacitor network 620 acts to average the switch output signal at node 613. The resistor capacitor network 620 produces an effective voltage which is ⅓ of the output of the operational amplifier 604. The output 613 is the amplification factor for the amplifier 604.

Filtering Unit

Figure 7:
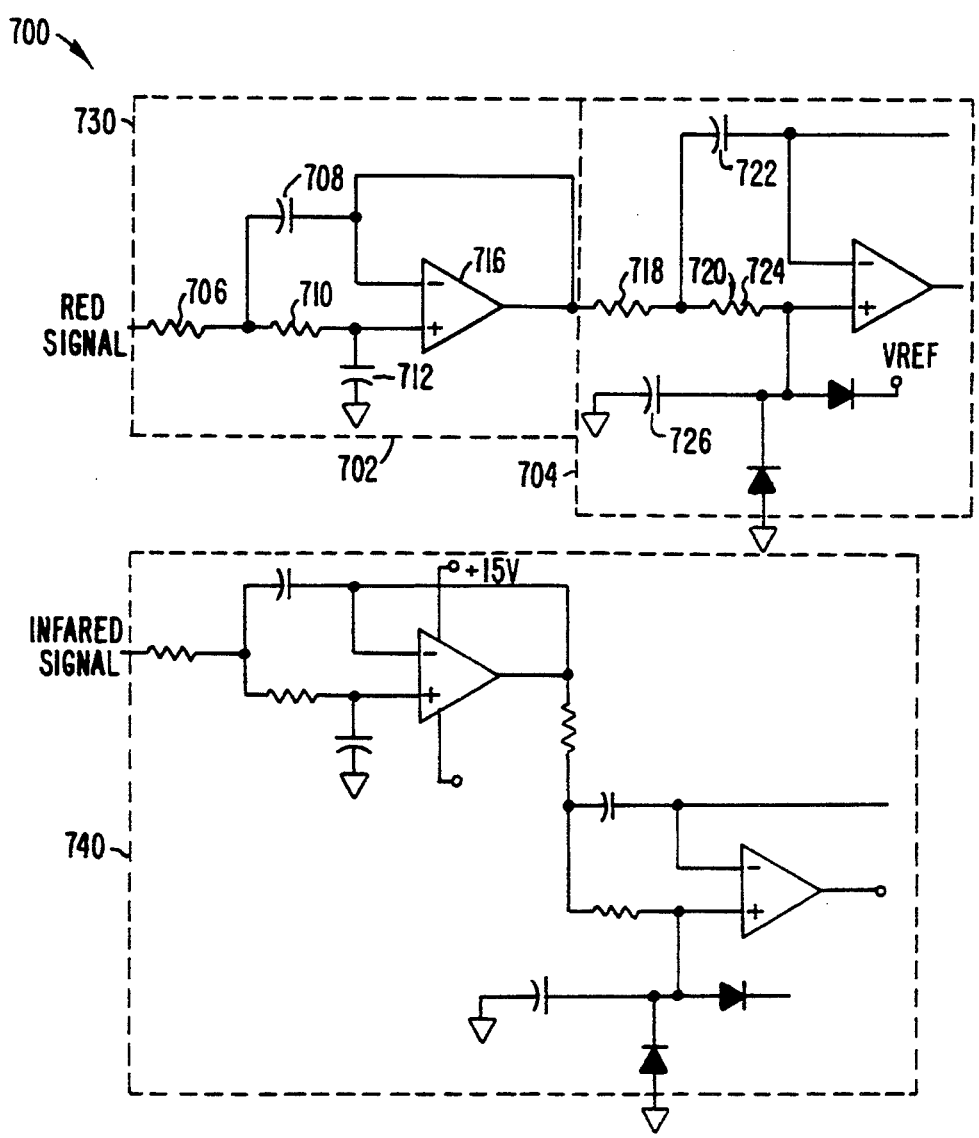
FIG. 7 is a circuit schematic of the Filtering Circuit of FIG. 2.

The output signal from the Variable Gain Amplification Unit 600 is filtered before being input into the Offset Subtractor Unit 800. FIG. 7 is a circuit schematic of the Filtering Unit 700 according to the present invention. The filtering unit 700 consists of two parallel two stage second order filters. A first two stage filter 730 is dedicated to filtering of the red LED signal; a second two stage filter 740 is dedicated to filtering the infrared LED signal. Both two stage filters 730 and 740 are functionally equivalent. The red LED two stage filter 730 is described for illustration purposes.

The output from amplifier 604 at node 612 is input into a first stage second order filter 702. The first stage filter is comprised of an amplifier 716, a series resistor 704 in parallel with a capacitor 708 and a resistor capacitor network including resistor 710 and capacitor 712. The resistor capacitor network is in parallel with the positive input terminal 714 of the inverting amplifier 716. The first stage filter 702 filters the input stage to reduce noise at the switching frequency.

A second stage filter is similarly comprised of an amplifier 730, a series resistor 270 in parallel with a capacitor 722 and a resistor capacitor network including a resistor 724 and a capacitor 726. The resistor capacitor network is in parallel with the positive input terminal 728 of the inverting amplifier 730. Similar to the first stage filter 702, the second stage filter 704 reduces noise at the switching frequency. In addition, a pair of diodes 732 and 734 are connected in parallel to the positive input terminal 728 of the inverting amplifier 730. The diode pair acts to limit the output voltage of the inverting amplifier 730 so that it does not exceed the range of the analog to digital converter by more than 0.7 volts.

The Offset Subtractor Circuit

Figure 8:
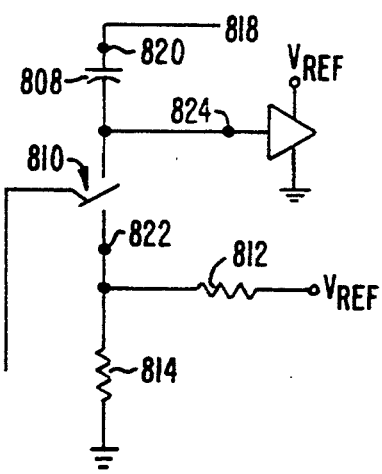
FIG. 8 is a circuit schematic of the Offset Subtractor Circuit of FIG. 2.

The Offset Subtractor Circuit eliminates the need for a 16 bit A/D converter by subtracting the DC offset from the combined waveform thus leaving the AC component of the waveform. FIG. 8 is a circuit schematic of the Offset Subtractor Circuit 800 according to the present invention. The Offset Subtractor Circuit 800 includes a first offset subtractor unit 802 for the subtraction of the DC component of the red LED signal and a second offset subtractor circuit 804 for subtraction of the DC component of the infrared LED signal. The first and second offset subtractor circuits are functionally equivalent. The red LED offset subtractor circuit is discussed for illustration purposes.

The Offset Subtractor Circuit 810 is comprised of a capacitor 808, a switch 810, and resistors 812 and 814. The combined waveform for the red LED signal is output from the filtering unit at node 816. The combined signal is split. The combined signal is input into the A/D converter along line 818 and input into capacitor 808.

Resistors 812 and 814 act as a voltage divider and provides a baseline voltage at node 822 which is approximately in the middle of the A/D converter range at 2.0 Volts in the absence of current through capacitor 808. This voltage position is important since the analog component of the waveform will vary in both the positive and negative directions around the reference voltage. Node 822 is tied to a reference voltage through resistor 812. When switch 810 is closed, capacitor 808 is charged to the voltage difference between node 820 and node 822. Thus the voltage at node 822 is equal to the voltage across capacitor 810 is the difference between the DC component and the baseline voltage.

When the switch 810 is opened, the voltage at node 822 is left at the differential voltage. Thus the voltage at node 824 will be equal to the combined AC and DC voltage minus whatever the combined DC voltage was at the instant the switch 810 was opened.

The microprocessor controls the switch timing so that the switch is closed immediately after each valley of the detector signal. The amount of time the switch is closed and the values of the capacitor and resistors are chosen so that the capacitor can charge in the interval the switch is closed. The microprocessor knows not to sample the signal during this interval.

The Second Variable Gain Amplifier

Figure 9:
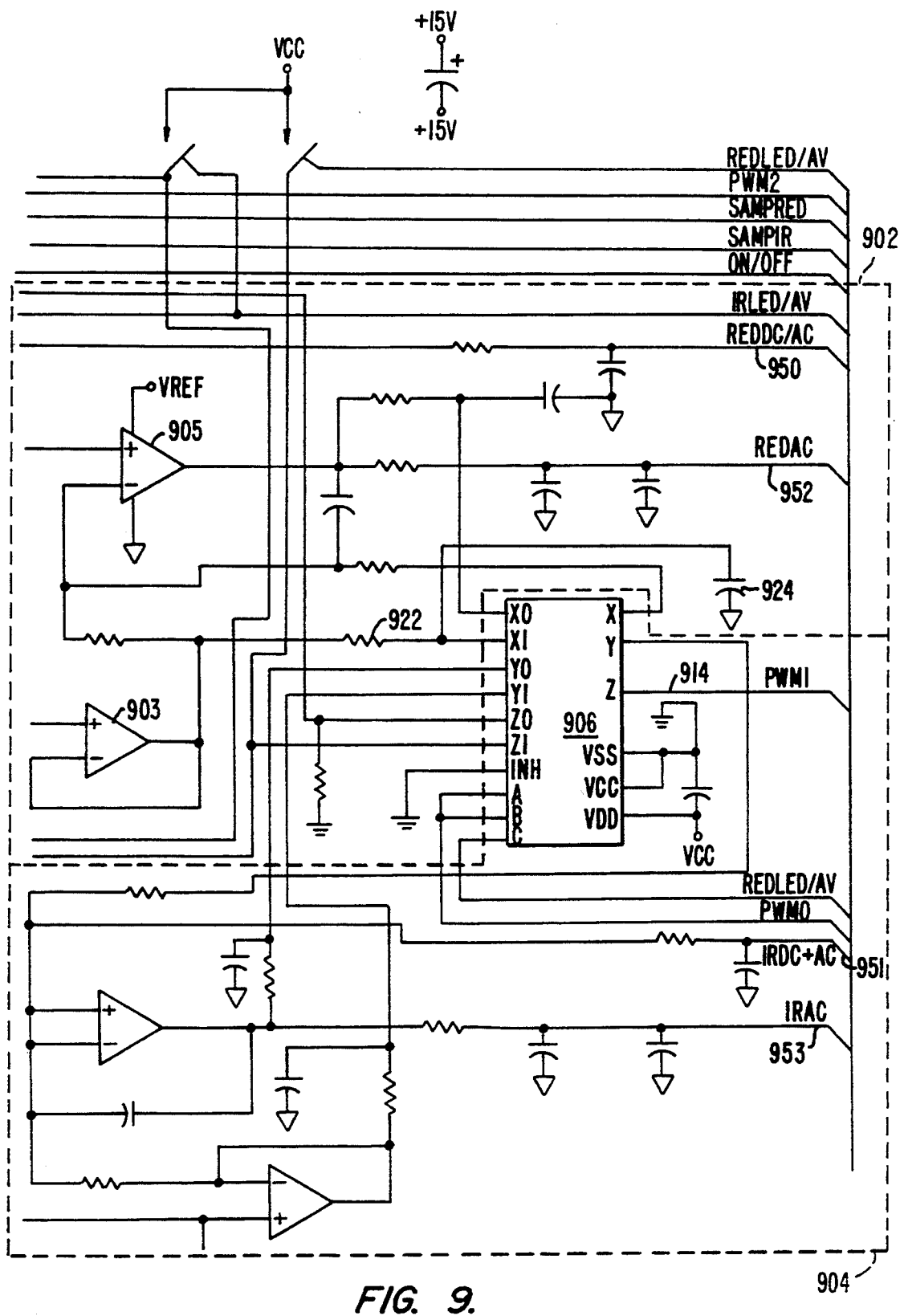
FIG. 9 is a circuit schematic of a Second Variable Gain Controlled Amplification Unit of FIG. 2.
Figure 10:
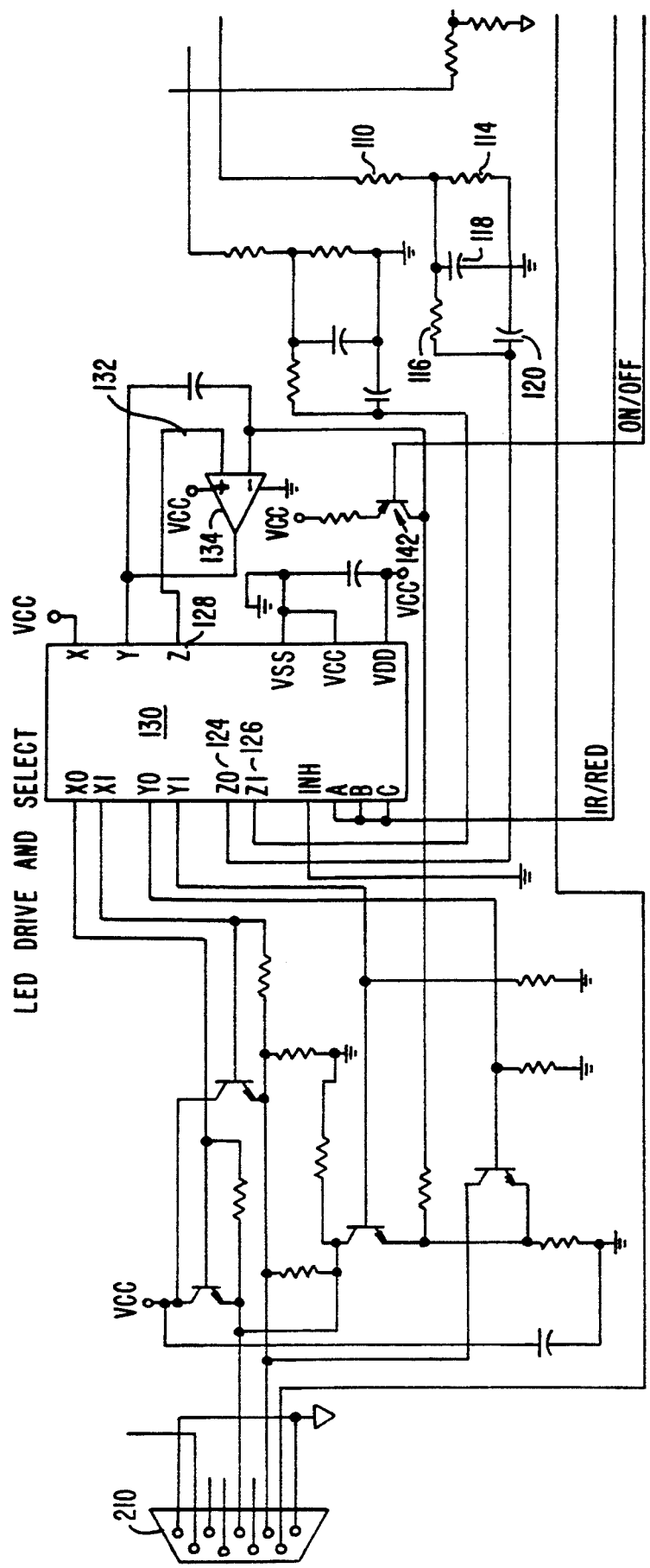
FIG. 10 is a circuit schematic of the LED Drive and Select Circuit of FIG. 2.

FIG. 9 is a circuit schematic of a Second Variable Gain Controlled Amplification Unit according to the present invention. The second variable gain amplification unit is comprised of an amplification unit 902 for the red LED signal and a second amplification unit 904 for the amplification of the infrared LED signal. Both amplifiers are functionally equivalent. The red amplification unit 902 is described for illustration purposes.

The Second Variable Gain Controlled Amplification Unit 900 is similar to the First Variable Gain Amplifier 600. First amplifier 600 amplified the combined DC and AC signal to the optimum level for the range of the A/D converter while second amplifier 900 amplifies the AC signal to the optimum level for the range of the A/D converter. The variable gain amplifier 900 amplifies the detected LED signals with the amount of amplification controlled by the pulse width modulator 991. The red variable gain amplification unit 902 is comprised of a pair of amplifiers 903 and 905 coupled to a switch 906 and a pair of resistor capacitor networks for filtering.

The output from both amplifiers 903 and 905 are input into a switch 906. The switch 906 contains three single pole double throw switches. The output of amplifier 903 is coupled to pole 908. The output of amplifier 905 is coupled to pole 910. In the First Variable Gain Amplification Unit 600, the switch 606 sequences the amplifier 604 between ground and the output of the amplifier. In the Second Variable Gain Amplification Unit 900 the switch sequences the amplifier 905 between a reference voltage of 2.0 volts and the output of the amplifier. The 2.0 volt reference voltage is buffered by the amplifier 903. Pole 908 is normally coupled to a reference voltage. Pole 910 is normally coupled to the output of the amplifier. Thus the output at pole 912 is alternately switched between ground and the amplifier output.

Switching between the output voltage of the amplifier and the reference voltage is controlled by the pulse width modulator 991 whose signal is input at node 914 of switch 906. The pulse width modulator signal controls how long the output on pin the pole 908 is connected to the reference voltage and how long the pole 910 is connected to the amplifier output. The pulse width modulator signal can be varied to effect how long the pulse width is on or off.

The switch output signal is input into a first resistor capacitor network comprised of a resistor 914 and a capacitor 918 which averages the signal to produce an effective voltage. In addition, a second resistor capacitor network comprised of a resistor 922 and a capacitor 924 is tied to the output of the amplifier 903 and the switch 906. It provides additional filtering before input into the switch 906.

The LED Drive & Select Circuit

The pulse width modulator 991 of the microprocessor 990 controls alternatively the amplification of the LED signal or the LED intensity, but not both. Typically upon initialization of the LED, the LED intensity is started at its minimum value. The LED intensity is increased until the signal is strong enough to see, and therefore be easily detectable by the photodetector. If increasing the intensity to its maximum does not give an adequate signal, the signal strength of the LED may be increased by increasing the gain of the amplifier by either the first or second variable gain amplifiers 600, 900.

The signal from the pulse width modulator on line 110 is input into a first resistor 112 and a resistor capacitor network comprised of resistors 114, 116 and capacitors 118, 120. The resistor capacitor network filters the signal. The signal on line 122 is proportional to the duty cycle of the pulse width modulator. If, for example, the pulse width modulator is at its lowest setting the output would be equal to 0.5 volts/256. This output signal on line 122 is used as a reference voltage.

The reference voltage is input into pole 124 of switch 130 which selects whether the reference voltage is used with respect to the infrared or red channel. If the red LED is to be turned on, then channel 124 will be selected and channel 128 will connect the noninverting input 132 of amplifier 134 to the reference voltage. The output 126 of the amplifier 134 is used to select the transistor, and thus the LED, the amplifier 134 will drive.

There is an LED Drive Circuit for both the red signal and infrared LED signals. Although the two driving circuits are functionally equivalent, the red signal drive circuit is discussed by way of example. If pole 124 is selected, the output of amplifier 134 will be connected to transistor 136. Transistor 136 is turned on when amplifier 134 is on and is producing sufficient current through resistor 138 that the voltage across resistor 140 is equal to the reference voltage. This creates a current into the LED which is proportional to the reference voltage.

To turn off the LED, transistor 142 is turned on. Turning on transistor 142, pulls up the inverting terminal of the amplifier 132 so that it is higher than the reference voltage. This turns off the amplifier 142 and thus the LED.

Algorithm for Calculation of Ratio of Ratios

The microprocessor 990 uses the separated AC and DC components of the measured signal to calculate the oxygen saturation content in the blood. The mathematical derivation for the Ratio of Ratios (RofR) is calculated using as a base the Beer-Lambert equation:

$$I_{out} = I_{in} e^{-CL[S\beta_o + [1-S]\beta_r]}$$

where $I_{out}$ is the current out of the photodetector, $I_{in}$ is the current into the light emitting diode (the red LED for RofR for the red wavelength, the IR LED for RofR for the IR wavelength), C is the concentration of the liquid (blood), L is the path length (between the LED and the photodetector), S is the Saturation, and $\beta_o$ and $\beta_r$ are material dependent constants.

By choosing two points in time you can eliminate the constant $I_{in}$ and arrive at:

$$I_{out}(t_o) = I_{out}(t_1) e^{-Cd[S\beta_o + [1-S]\beta_r]}$$

where $d = L(t_o)$ and is equal to the difference in path length between the two times $t_o$ and $t_1$. In existing methods $t_o$ is measured at the peak of the waveform and $t_1$ is measured at the valley of the waveform.

Dividing both sides by $I_{out}(t_1)$ and taking the natural logarithm gives $$\ln \frac{I_{out}(t_o)}{I_{out}(t_1)} = -Cd[S\beta_o + [1-S]\beta_r]$$

This is the function at one wavelength, so using both wavelengths and dividing the results yields the Ratio of Ratios.

$$RofR = \frac{\ln \frac{(I_{out}(t_o)\lambda_2)}{(I_{out}(t_1)\lambda_2)}}{\ln \frac{(I_{out}(t_o)\lambda_1)}{(I_{out}(t_1)\lambda_1)}} = \frac{-Cd[S\beta_o\lambda_2 + [1-S]\beta_r\lambda_2]}{-Cd[S\beta_o\lambda_1 + [1-S]\beta_r\lambda_1]}$$

The Ratio of Ratios is typically calculated by taking the natural logarithm of the ratio of the peak value of the red signal divided by valley measurement of the red signal. The aforementioned value is then divided by the natural logarithm of the ratio of the peak value of the infrared signal divided by the value of valley measurement of the infrared signal.

Since the concentration "C" is the same for both wavelengths it cancels out. In addition, the difference or "change" in path lengths is the same for both channels, so it also cancels out. Thus the Ratio of Ratios may be calculated according to the following formula.

$$RofR = \frac{[S\beta_o\lambda_2 + [1-S]\beta_r\lambda_2]}{[S\beta_o\lambda_1 + [1-S]\beta_r\lambda_1]}$$

In the present invention, the Ratio of Ratios is determined using derivatives. Assuming the change in path length is the same for both wavelengths during same time interval between samples, the instantaneous change in path length (dL/dt) must also be the same for both wavelengths. Thus the same Ratio of Ratios can be derived by taking the derivative of $I_{out}$. This can be shown mathematically by the same process that was used to derive Ratio of Ratios:

$$I_{out} = I_{in} e^{-CL[S\beta_o + [1-S]\beta_r]}$$

Since $$\frac{de^u}{dt} = \frac{e^u du}{dt}$$

and $I_{in}$ is constant $$\frac{dI_{out}}{dt} = I_{in} e^{-CL[S\beta_o + [1-S]\beta_r]} (-CdL[S\beta_o + [S-1]\beta_r])$$

Dividing $$\frac{dI_{out}}{dt}$$

by $I_{out}$ yields $$\frac{\frac{dI_{out}}{dt}}{I_{out}} = \frac{I_{in}e^{-CL[S\beta_o+[1-S]\beta_r]}\left(\frac{-CdL}{dt}[S\beta_o + [1-S]\beta_r]\right)}{I_{in}e^{-CL[S\beta_o+[1-S]\beta_r]}}$$

therefore $$\frac{\frac{dI_{out}}{dt}}{I_{out}} = \frac{-CLdL}{dt}[S\beta_o + [1-S]\beta_r]$$

using two wavelengths and dividing gives $$\frac{\frac{dI_{out}\lambda_2}{dt}}{\frac{I_{out}\lambda_2}{\frac{dI_{out}\lambda_1}{dt}}} = \frac{\frac{-CdL}{dt}[S\beta_o\lambda_2 + [1-S]\beta_r\lambda_2]}{\frac{-CdL}{dt}[S\beta_o\lambda_1 + [1-S]\beta_r\lambda_1]}$$

Since we know that the change in the path length (dl/dt) is the same for both wavelengths, this cancels out giving:

$$\frac{\frac{dI_{out}\lambda_2}{dt}}{\frac{I_{out}\lambda_2}{\frac{dI_{out}\lambda_1}{dt}}} = \frac{[S\beta_o\lambda_2 + [1-S]\beta_r\lambda_2]}{[S\beta_o\lambda_1 + [1-S]\beta_r\lambda_1]}$$

rearranging the formula gives:

$$\frac{I_{out}\lambda_1 \frac{dI_{out}\lambda_2}{dt}}{I_{out}\lambda_2 \frac{dI_{out}\lambda_1}{dt}} = RofR$$

where $l_{out}$ is equal to the combined AC and DC component of the waveform and $$\frac{dI_{out}}{dt}$$

is equal to the derivative of the and AC component of the waveform. Thus the same equation for Ratio of Ratios can be derived by taking the derivative of the Beer-Lambert function. Instead of using the previous method of calculating the Ratio of Ratios based on the natural logarithm of the peak and valley values of the red and infrared signals, the value RofR can be calculated based on the derivative value of the AC component of the waveform.

To calculate the Ratio of Ratios according to the derivative based formula, a large number of sampled points along the waveform are used instead of merely the peak and valley measurements. A series of sample points from the digitized AC and AC+DC values for the infrared and red signals are used to form each data point. A digital FIR filtering step essentially averages these samples to give a data point. A large number of data points are determined in each period. The period is determined after the fact by noting where the peak and valley occurs.

For the AC signal, a derivative is then calculated for each pair of data points and used to determine the ratio of the derivatives for red and IR. A plot of these ratios over a period will ideally result in a straight line. Noise from motion artifact and other sources will vary some values. But by doing a linear regression, a best line through a period can be determined, and used to calculate the Ratio of Ratios.

A problem with prior systems was DC drift. In prior methods, a linear extrapolation was performed between two consecutive negative peaks of the waveform. This adjusts the negative peak of the waveform as if the shift due to system noise did not occur. A similar correction can be calculated using the derivative form of the waveform. In performing the correction of the DC component of the waveform, we assume that the drift caused by noise in the system is so much slower than the waveform pulses that the drift is linear. The linear change on top of the waveform can be described by the function:

$$f(x) = f(x) + mx + b$$

where m is equal to the slope of the waveform and B is equal to a constant.

The linear change added to the waveform doesn't affect the instantaneous DC component of the waveform. However, the derivative of the linear change will have an offset due to the slope of the interferring signal:

$$\frac{d(f(x) + mx + b)}{dt} = \frac{df(x)}{dt} + m$$

If we assume that the offset is constant over the period of time interval, then the Ratio of Ratios may be calculated by subtracting the offsets and dividing:

$$\frac{I_{out}\lambda_1 \frac{(dI_{out}\lambda_2)}{dt}}{I_{out}\lambda_2 \frac{(dI_{out}\lambda_1)}{dt}} = \frac{Y}{X}$$

$$RofR = \frac{Y - m_2}{X - m_1}$$

where "y" and "x" are the original values and $m_1$ and $m_2$ are the offsets.

Since the Ratio of Ratios is constant over this short time interval the above formula can be rewritten as $$\frac{y - m_2}{x - m_1} = R$$

$$y - m_2 = R(x - m_1) \quad y = Rx - Rm_1 + m_2$$

therefore $$y = Rx + (m_1 + Rm_1)$$

Since we have assumed $m_1$, $m_2$, and R are constant over the time interval, we have an equation in the form of $y = mx + b$ where the m is the Ratio of Ratios. Thus, we do a large number of calculations of the Ratio of Ratios for each period, and then do the best fit calculation to the line $y = Rx + b$ to determine the optimum value of R for that period, taking into account the constant b which is caused by DC drift.

To determine the Ratio of Ratios exclusive of the DC offset we do a linear regression over the data points. In performing a linear regression, it is preferred to take 5 points along the curve having a large differential component, for example, from peak to valley. This will cause the mx term to dominate the constant b.

$$R = \frac{n\Sigma x_j y_j - \Sigma x_j \Sigma y_j}{n\Sigma x_j^2 - (\Sigma x_j)^2}$$

where
n = # of samples
j = sample #

$$x = I_{red}\frac{dI_{IR}}{dt}$$

$$y = I_{IR}\frac{dI_{RED}}{dt}$$

Prior sampling methods typically calculate the Ratio of Ratios by sampling the combined AC and DC components of the waveform at the peak and valley measurements of the waveform. Sampling a large number of points on the waveform, using the derivative and performing a linear regression increases the accuracy of the Ratio of Ratios, since noise is averaged out. The derivative form eliminates the need to calculate the logarithm. Furthermore doing a linear regression over the sample points not only eliminates the noise caused by patient movement of the oximeter, it also decreases waveform noise caused by other sources.

Although the invention has been explained by referenced to the foregoing embodiment, it should be understood that the above description is merely illustrative and is provided for example only. Thus it should be understood that the invention is limited only in accordance with the appended claims.

What is claimed is:

1. A method for determining a parameter of blood, comprising the steps of:
    emitting first and second wavelengths of light through a sample;
    detecting said first and second wavelengths of light through said sample;
    producing first and second analog signals responsive to said detection of said first and second wavelengths, respectively, said first and second analog signals being proportional to the intensity of said first and second wavelengths of light, respectively, said first analog signal having an AC and DC component and said second analog signal having an AC and a DC component;
    separating said AC component of said first analog signal from said first analog signal to produce a first separated AC component and separating said AC component of said second analog signal from said second analog signal to produce a second separated AC component;
    converting said first and second separated AC components into a first digital signal and a second digital signal, respectively;
    computing the derivatives of said first and second separated AC components;
    taking a linear regression of the ratio of said derivatives of said first and second separated AC components for a plurality of sample points in a period; and
    computing said parameter of blood, said parameter of blood being dependent on the derivatives of said first and second separated AC components.

2. The method of claim 1 wherein an A/D converter having an input voltage range is used for said converting step, the method further comprising the steps of amplifying said first and second analog signals to be in said range, wherein said first analog signal is amplified at a different level than said second analog signal.

3. The method of claim 1 wherein an A/D converter having an input voltage range is used for said converting step, the method further comprising the step of amplifying said first and second separated AC components to be in said range.

4. The method as recited in claim 3, wherein the amount of amplification of said first and second separated AC components is controlled by a pulse width modulator, wherein the length of the pulse of said pulse width modulator is proportional to the amount of amplification of said first and second separated AC components.

5. The method as recited in claim 1, further comprising the step of increasing the intensity of said first wavelength of light such that said first analog signal is in the range of an A/D converter used for said converting step.

6. The method as recited in claim 5, wherein the intensity of said first wavelength of light is controlled by a pulse width modulator.

7. The method as recited in claim 1, wherein the step of separating the AC component from said first and second analog signals includes,
    periodically charging first and second capacitors to approximately the value of said DC component of said first and second analog signals, respectively; and
    subtracting the DC component stored on said capacitors from said first and second analog signals, respectively.

8. The method recited in claim 7 wherein charging of said first and second capacitors is controlled by a microprocessor controlled switch.

9. The method as recited in claim 1, wherein said derivatives of said first and second separated AC components are calculated from the change in value between consecutive digital sample points in a period.

10. The method as recited in claim 1, further comprising the step of converting said first and second analog signals into a third and fourth digital signal, respectively.

11. The method as recited in claim 10, wherein said step of computing said parameter of the blood is calculated using the relationship $$\frac{I_{out}\lambda_1 \frac{dI_{out}\lambda_2}{dt}}{I_{out}\lambda_2 \frac{dI_{out}\lambda_1}{dt}} = RofR$$

where $I_{out}\lambda_1$ is equal to said third digital signal, $I_{out}\lambda_2$ is equal to said fourth digital signal, $$\frac{dI_{out}\lambda_1}{dt}$$

represents the derivative of said first separated AC component, and $$\frac{dI_{out}\lambda_2}{dt}$$

represents the derivative of said second separated AC component.

12. The method as recited in claim 1, wherein the parameter of the blood is the oxygen saturation level.

13. The method as recited in claim 1, wherein said first and second wavelengths of light are in the infrared and red regions, respectively.

14. The method as recited in claim 1 further comprising adding a fixed DC offset to said first and second separated AC components, wherein the sum of said fixed DC offset and said first separated AC component and the sum of said fixed DC offset and said second separated AC component are in the middle of an input voltage range of said A/D converter.

15. An apparatus for measuring a parameter of the blood, comprising:
a first and second light emitting means for emitting first and second wavelengths of light, respectively, said first and second light emitting means directing light through a sample;
means responsive to said first and second light emitting means for detecting said first and second wavelengths of light transmitted through said sample, said detection means including a photodetector, said detection means producing first and second analog signals, said first and second analog signals being proportional to the intensity of said first and second wavelengths of light, respectively, said first and second analog signals each having an AC and a DC component;
means for separating said AC component of said first analog signal from said first analog signal to produce a first separated AC component and separating said AC component of said second analog signal from said second analog signal to produce a second separated AC component, wherein said means for separating includes a subtractor circuit;
an analog to digital converter, coupled to said means for separating, said converter converting said first separated AC component into a first digital signal and said second separated AC component into a second digital signal, said analog to digital converter having an input voltage range; and
means for taking a linear regression of the ratio of derivatives of said first and second separated AC components for a plurality of sample points in a period, said means for taking a linear regression including a microprocessor which computes said parameter of blood from said first and second digital signals, wherein the value of said parameter of blood is dependent on the derivative of said first separated AC component and the derivative of said second separated AC component.

16. The apparatus of claim 15, further comprising an amplifier which amplifies said first and second analog signals to be in the range of said analog to digital converter, wherein said first analog signal is amplified at a different level than said second analog signal.

17. The apparatus of claim 15, further comprising an amplifier which amplifies said first and second separated AC components to be in the range of said analog to digital converter.

18. The apparatus of claim 15, further comprising a pulse width modulator, wherein said pulse width modulator controls an amount of amplification of said first and second separated AC components, wherein the pulse length of said pulse width modulator is proportional to the amount of amplification of said first and second separated AC components.

19. The apparatus recited in claim 15, further comprising a means for increasing the intensity of said first wavelength of light such that said first analog signal is in the range of said analog to digital converter.

20. The apparatus recited in claim 15, wherein the means for separating said AC component from said first and second analog signals includes,
first and second capacitors, said first and second capacitors periodically charging to approximately the value of the DC component of said first and second analog signals, respectively.

21. The apparatus recited in claim 20 further comprising a microprocessor controlled switch, wherein charging of said first and second capacitors is controlled by said microprocessor controlled switch.

22. The apparatus recited in claim 15, wherein said means for taking a linear regression calculates said derivatives of said first and second separated AC components from a change in value between two consecutive digital sample points in the period.

23. The apparatus recited in claim 15, wherein said analog to digital converter converts said first and second analog signals into a third and fourth digital signal, respectively.

24. The apparatus as recited in claim 22, wherein said means for taking a linear regression calculates said parameter of the blood in said microprocessor according to the relationship $$\frac{I_{out}\lambda_1 \frac{dI_{out}\lambda_2}{dt}}{I_{out}\lambda_2 \frac{dI_{out}\lambda_1}{dt}} = RofR$$

where $I_{out}\lambda_1$ is equal to said third digital signal, $I_{out}\lambda_2$ is equal to said fourth digital signal, $$\frac{dI_{out}\lambda_1}{dt}$$

represents the derivative of said first separated AC component, and $$\frac{dI_{out}\lambda_2}{dt}$$

represents the derivative of said second separated AC component.

25. The apparatus recited in claim 15, wherein said apparatus measures the oxygen saturation level.

26. The apparatus recited in claim 15, wherein said first and second light emitting means emit first and second wavelengths of light in the infrared and red regions, respectively.

27. The apparatus recited in claim 15 wherein said analog to digital converter has a range, further comprising means for adding a fixed DC offset to said first and second separated AC components, wherein the sum of said fixed DC offset and said first separated AC component and the sum of said fixed DC offset and said second separated AC component are in the middle of an said range.

28. A method for determining a parameter of blood, comprising the steps of:
   emitting first and second wavelengths of light through a sample;
   detecting said first and second wavelengths of light through said sample;
   producing first and second analog signals responsive to said detection of said first and second wavelengths, respectively, said first and second analog signals being proportional to the intensity of said first and second wavelengths of light, respectively, said first analog signal having an AC and DC component and said second analog signal having an AC and a DC component;
   separating said AC component of said first analog signal from said first analog signal to produce a first separated AC component and separating said AC component of said second analog signal from said second analog signal to produce a second separated AC component;
   converting said first and second separated AC components into a first digital signal and a second digital signal, respectively, using an A/D converter having an input voltage range;
   amplifying said first and second separated AC components to be in the range of the A/D converter used for the converting step, wherein the amount of amplification of said first and second separated AC components is controlled by a pulse width modulator, wherein the pulse length of said pulse width modulator is proportional to the amount of amplification of said first and second separated AC components;
   computing the derivative of said first and second separated AC components; and
   computing said parameter of blood, said parameter of blood being dependent on the value of said first and second digital signals.

29. A method for determining a parameter of blood, comprising the steps of:
   emitting first and second wavelengths of light through a sample;
   detecting said first and second wavelengths of light through said sample;
   producing first and second analog signals responsive to said detection of said first and second wavelengths, respectively, said first and second analog signals being proportional to the intensity of said first and second wavelengths of light, respectively, said first analog signal having an AC and DC component and said second analog signal having an AC and a DC component;
   separating said AC component of said first analog signal from said first analog signal to produce a first separated AC component and separating said AC component of said second analog signal from said second analog signal to produce a second separated AC component;
   converting said first and second separated AC components into a first digital signal and a second digital signal, respectively, using an A/D converter having an input voltage range wherein the intensity of said first wavelength of light is increased such that said first analog signal is in the range of the A/D converter;
   computing the derivative of said first and second separated AC components;
   taking a linear regression of the ratio of said derivatives of said first and second separated AC components for a plurality of sample points in a period; and
   computing said parameter of blood, said parameter of blood being dependent on the value of said first and second digital signals.

30. A method for determining a parameter of blood, comprising the steps of:
   emitting first and second wavelengths of light through a sample;
   detecting said first and second wavelengths of light through said sample;
   producing first and second analog signals responsive to said detection of said first and second wavelengths, respectively, said first and second analog signals being proportional to the intensity of said first and second wavelengths of light, respectively, said first analog signal having an AC and DC component and said second analog signal having an AC and a DC component;
   periodically charging first and second capacitors to approximately the value of said DC component of said first and second analog signals, respectively;
   subtracting the DC component values to which said capacitors are charged from said first and second analog signals, respectively, to produce a first separated AC component and a second separated AC component;
   converting said first and second separated AC components into a first digital signal and a second digital signal, respectively;
   computing the derivative of said first and second separated AC components; and
   computing said parameter of blood, said parameter of blood being dependent on the value of said first and second digital signals.

* * * * *